United States Patent [19]

Suehiro, deceased et al.

[11] Patent Number: 5,051,362

[45] Date of Patent: Sep. 24, 1991

[54] ENZYME IMMOBILIZED BY SPRAY-DRYING AND PHOTOCROSSLINKING A POLY(VINYL ALCOHOL) POLYMER

[75] Inventors: Tetsuro Suehiro, deceased, late of Tokyo, by Keiko Suehiro, executor; Kunihiro Ichimura, Tsukuba, both of Japan

[73] Assignee: Agency of Industrial Science & Technology Ministry of International Trade & Industry, Tokyo, Japan

[21] Appl. No.: 322,724

[22] Filed: Mar. 13, 1989

[30] Foreign Application Priority Data

Mar. 31, 1988 [JP] Japan .................................. 63-79676

[51] Int. Cl.$^5$ ...................... C12N 11/04; C12N 11/08
[52] U.S. Cl. .................................. 435/182; 435/180; 530/817
[58] Field of Search ............... 435/174, 177, 180, 182; 530/817

[56] References Cited

U.S. PATENT DOCUMENTS

| | | | |
|---|---|---|---|
| 4,061,466 | 12/1977 | Sjoholm et al. | 435/182 X |
| 4,205,128 | 5/1980 | Ishimatsu et al. | 435/182 |
| 4,272,620 | 6/1981 | Ichimura | 430/287 X |
| 4,898,781 | 2/1990 | Onouchi et al. | 435/182 X |

FOREIGN PATENT DOCUMENTS 128888 10/1986 Japan .................................. 435/182

*Primary Examiner*—David M. Naff
*Attorney, Agent, or Firm*—Oblon, Spivak, McClelland, Maier & Neustadt

[57] ABSTRACT

Enzyme-occluding polymer particles are produced by a method including the steps of dissolving an enzyme in an aqueous solution of poly(vinyl alcohol) possessing a styrylpyridinium group or a styrylquinolinium group, spray drying the aqueous solution, and exposing the resultant dry particles to an actinic ray, thereby photocrosslinking the particles.

11 Claims, No Drawings

ENZYME IMMOBILIZED BY SPRAY-DRYING AND PHOTOCROSSLINKING A POLY(VINYL ALCOHOL) POLYMER

BACKGROUND OF THE INVENTION

1. Field of the Invention

This invention relates to minute polymer particles having an enzyme immobilized therein and a method for the production thereof. More particularly, this invention relates to minute enzyme-occluding polymer particles having an occluded enzyme with a photo-crosslinking resin and possessing an excellent enzymatic activity and to a method for the production thereof.

2. Prior Art Statement

Heretofore, it has been known that the production of polymer particles having an enzyme immobilized therein is attained by a method which comprises dissolving the enzyme in an aqueous solution of poly(vinyl alcohol) or a derivative thereof and exposing the enzyme-containing aqueous solution to radiation thereby crosslinking the poly(vinyl alcohol) or the derivative thereof and, at the same time, immobilizing the enzyme therein [Japanese Patent Publication SHO 56(1981)-33 and Japanese Patent Publication SHO 59(1984)-13189].

Since this method requires use of radiation, however, it necessitates installation of a special apparatus and entails the possibility of the enzyme being degenerated. Thus, many problems still stand in the way of rendering this method commercially feasible.

Several methods have been known which effect the immobilization of an enzyme by the use of a photosensitive resin [Japanese Patent Public Disclosure SHO 53(1978)142594 and Japanese Patent Public Disclosure SHO 55(1980)15703].

In these methods, however, since the enzyme is immobilized in the resin which is formed in the shape of film, particles, or fibers, only the part of the enzyme exposed from the surface of the shaped article of resin actually participates in the reaction intended. As a result, the amount of enzyme which is utilized is inevitably very small as compared with the amount of enzyme immobilized.

Formerly, the inventors proposed a method for forming enzyme-occluding polymer particles preparing an enzyme-containing aqueous solution of a styrylpyridinium group-containing poly(vinyl alcohol) as a water-soluble photosensitive resin and subjecting the aqueous solution as dispersed in a hydrophobic medium to photo-crosslinking Japanese Patent Public Disclosure SHO 61(1986)-128888].

By this proposed method are obtained enzyme-occluding polymer particles 20 to 100 μm in average particle diameter having the enzyme immobilized in such a state that the enzyme may manifest its function efficiently without a sacrifice of its activity.

The enzyme-occluding polymer particles obtained this proposed method, however, have a relatively large average particle diameter in the range of 20 to 100 μm and are not fully satisfactory in terms of manifestation of enzymatic activity.

Further, the method itself is deficient in capacity for mass production because the aqueous solution is subjected to the photo-crosslinking as held in a stirred state and the production, therefore, is performed batchwise. Moreover, the dosage of radiation is lowered because the aqueous solution is exposed to light as held in a dispersed state and the photosensitivity is degraded because the enzyme and the resin are in a wet state.

Besides, since the particles obtained by the crosslinking are in a wet state, they must be dried prior to their use in a non-aqueous type enzymatic reaction. When they are dried, there ensues a disadvantage that they undergo conglomeration due to cohesion of adjacent particles. The particles fresh from production are wet with suspended substances adhering to their surface and, therefore, must be washed as with a solvent.

OBJECT AND SUMMARY OF THE INVENTION

An object of this invention is to provide enzyme-occluding polymer particles possessing a small average particle diameter and exhibiting a high activity and a method for the production thereof. Another object of this invention is to provide enzyme-occluding polymer particles allowing production by a continuous process, requiring no aftertreatment, and highly suitable for quantity production and a method for the production thereof.

To accomplish the objects described above, the present invention obtains enzyme-occluding polymer particles by dissolving a given enzyme in an aqueous solution of poly(vinyl alcohol) possessing a styrylpyridinium group or a styrylquinolinium group, subsequently spray drying the resultant enzyme-containing aqueous solution, and exposing the spray dried particles to an actinic ray thereby photo-crosslinking the resin.

In the present invention, since the enzyme-containing aqueous solution is spray dried as described above, the produced polymer particles readily acquire an average particle diameter in the range of 0.5 to 10 μm and the production of the polymer particles can be performed by a continuous process suitable for quantity production. Further, since the polymer particles are obtained in a dry state, the photo-crosslinking proceeds efficiently and the method excels in productivity.

The other objects and characteristics of the present invention will become apparent from the following detailed description.

DETAILED DESCRIPTION OF THE PREFERRED EMBODIMENT

As already described, the inventors formerly proposed a method for forming enzyme-occluding polymer particles by preparing an enzyme-containing aqueous solution of styrylpyridinium group-containing poly(vinyl alcohol) as a water-soluble photosensitive resin and subjecting the aqueous solution as dispersed in a hydrophobic medium to photo-crosslinking. They continued study and experimentation and found that minute enzyme-occluding polymer particles are continuously obtained in a dry state by dissolving a given enzyme in an aqueous solution of styrylpyridinium group- or styrylquinolinium group-containing poly(vinyl alcohol), then spray drying the enzyme-containing aqueous solution, and subjecting the resultant minute dry particles to photo-crosslinking. The present invention has issued from this finding.

The poly(vinyl alcohol) possessing a styrylpyridinium group or styrylquinolinium group which is used in this invention is a well-known substance. For example, it can be produced by causing poly(vinyl alcohol) or partially saponified poly(vinyl acetate) to react with a styrylpyridinium salt represented by the following general formula or a styrylquinolinium salt [Japanese Patent Publication SHO 56(1981)-5761].

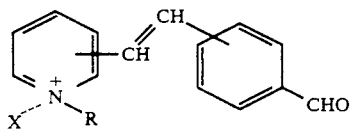

In the general formula, R stands for a hydrogen atom, a substituted or un-substituted alkyl group, aryl group, or aralkyl group such as, for example, a lower hydroxyalkyl group and X⁻ stands for the anion of a strong acid.

In the formula given above, the pyridine ring or benzene ring may possess a substituent and the pyridine ring may possess a condensed benzene ring and form a quinoline ring.

Suitably the poly(vinyl alcohol) or the partially saponified poly(vinyl acetate) to be used herein has a polymerization degree in the range of 500 to 3,000. When the partially saponified poly(vinyl acetate) is used, it is desired to have a saponification ratio in the range of 70 to 88%.

If the polymerization degree is less than 500, the aqueous solution does not produce desirable particles when it is photo-crosslinked. If the polymerization degree is larger than 3,000, or if the saponification ratio of the poly(vinyl acetate) is less than 70%, the resin becomes an insolubilized substance and does not form desirable particles.

By the same token, the styrylpyridinium group and/or styrylquinolinium group is desired to be incorporated in a ratio in the range of 0.5 to 8 mol %, based on the vinyl alcohol unit.

The immobilization to be effected in the present invention has no need for such conditions as exposure to radiation, application of heat, and use of a crosslinking agent, which have adverse effects on enzymes. Thus, the present invention is not particularly restricted by the kind of enzyme to be immobilized.

Examples of the enzyme effectively immobilized by this invention include hydrolases such as amylase, protease, cellulase, hemicellulase, lipase, pectinase, lysozyme, naringinase, hesperidinase, anthocyanase, aminoacylase, urease, invertase, melibiase, dextranase, peptidase, ribonuclease, and lactase, oxidoreductases such as glucose oxidase, uricase, catalase, riboxygenase, lipoxigenase, cytochrome C, and peroxidase, isomerases such as glucose isomerase, transferases such as cyclodextrin glucosyl transferase and transamynase, and eliminases such as aspartase, hierourondase, chondroitinase, and pectin eliminase.

To work the method of this invention advantageously, a poly(vinyl alcohol) possessing a styrylpyridinium group or styrylquinolinium group is dissolved in water in a concentration in the range of 0.1 to 5%, preferably 0.2 to 3%. Then, in the resultant aqueous solution, a given enzyme is thoroughly stirred.

Suitably, the amount of the enzyme to be used is approximately in the range of 5 to 50% by weight, based on the amount of the poly(vinyl alcohol).

Then, the resultant enzyme-containing aqueous solution is spray dried.

This spray drying is attained efficiently with a spray drier. The spray nozzle of the spray drier is desired to be of a two-fluid nozzle type to ensure generation of minute spray droplets. When a large spray drier is to be employed, it may be an airless spray or a rotary disc type spray.

Then, the spray drying is desired to be so regulated that the spray droplets will may have an average diameter of not more than 50 μm, preferably not more than 20 μm.

The initial temperature of the current of air used for the spray drying is desired to fall approximately in the range of 30° to 80° C. Even at this temperature of the drying air current, the temperature of the spray droplets is retained at the wet-bulb temperature and the drying is attained within a period on the order of seconds. The enzyme, therefore, does not yield to thermal degeneration.

Generally, an air current may be used satisfactorily as the drying current. The amount of the air current and the amount of spray can be easily determined empirically so as to produce spray droplets of the aforementioned diameter.

The particles formed by the spray drying and then collected as with a cyclone are exposed to an actinic ray to be photo-crosslinked.

The exposure to the actinic ray to be performed in this case is accomplished by the use of any of the conventional light sources resorted to in the photosetting of an ordinary sensitive material. The light sources which are available therefor include a high-pressure mercury-vapor lamp, a xenone lamp, a metal halide lamp, an arc lamp, a fluorescent lamp, a tungsten lamp, an argon ion laser, and a helium cadmium laser. On exposure to this actinic ray, the poly(vinyl alcohol) possessing a styrylpyridinium or styrylquinolinium group is photo-crosslinked to form polymer particles. This photo-crosslinking reaction is generally completed in several minutes to some tens of minutes, though variable more or less with the kind of resin to be used or the conditions of crosslinking.

As a result of the photo-crosslinking reaction, there are obtained polymer particles possessing an average particle diameter in the range of 0.1 to 10 μm, preferably 0.1 to 5 μm, and carrying the enzyme at a rate in the range of 5 to 50% by weight.

The enzyme-occluding polymer particles obtained as described above, similarly to the conventional immobilized enzyme, can be utilized for various enzymatic reactions by a method which comprises filling a column with the polymer particles and allowing a substrate-containing solution to flow down the packed column or a method which comprises stirring the polymer particles in combination with a substrate-containing solution added thereto.

The polymer particles, when necessary, may be converted into minute particles by pelletization using a binder. To be specific, the polymer particles are rotated in a pelletizer and, at the same time, an aqueous solution of a water-soluble polymer is sprayed on the polymer particles in motion. Owing to the action of the polymer, the polymer particles are conglomerated to form minute porous particles.

As the binder for the secondary pelletization, the polymer used as the raw material for the polymer particles of this invention may be used. Some other binder may be used which has no adverse effect on the enzyme and the polymer being used and on the enzymatic reaction intended to be produced. Examples of the binder meeting this description are polysaccharides such as alginic acid and carrageenin.

Further, while the powder obtained by drying the liquid polymer/enzyme mixture has not yet been exposed to light for the purpose of photo-crosslinking, the secondary pelletization of this powder can be carried out by using water in place of the binder.

It is also permissible to carry out the secondary pelletization by exposure to an actinic ray during or after the photo-crosslinking effected by exposure to an actinic ray.

As a result, there are obtained porous secondary particles. Thus, there are produced enzyme-occluding polymer particles of a large diameter which have a large surface area for contact with a reactive substrate, exhibit very high activity, and suffer from only small pressure loss.

The particles obtained by the pelletization are allowed to acquire large diameters up to about several mm. The secondary particles can be produced with a porosity which can be controlled approximately in the range of 20 to 60%.

In accordance with this invention, very minute enzyme-occluding polymer particles having an average particle diameter of 0.5 to 10 $\mu$m are obtained. These polymer particles exhibit very high activity.

The method of this invention excels in productivity because it can effect the production aimed at by a continuous process.

Further, since the particles are obtained in a dry state, the efficiency of photo-crosslinking is high. Owing to the dryness of the produced particles, the otherwise indispensable removal of a suspending medium, for example, adhering to the particle surface is no longer necessary. This fact adds to the productivity of the method of the present invention.

When the particles of this nature are subjected to the secondary pelletization, there are obtained particles possessing a large diameter, exhibiting high activity, and suffering from only small pressure loss.

The secondary pelletized particles of this invention are dried in an overwhelmingly short span of time on the order of seconds as compared with what is involved in the method which comprises casting an enzyme-containing solution onto a flat surface of a substrate, drying the solution on the flat surface to form a film thereon and then exposing the film to light and which uses the same polymer as the present invention as disclosed in Japanese Patent Public Disclosure SHO 55(1980)-23941. Owing to the briefness of the drying time, the particles do not yield to the phase separation between the enzyme and the polymer which could possibly occur during the course of air drying and, therefore, are allowed to form a uniform meshwork of polymer, with the enzyme uniformly dispersed within the meshwork. As a result, the ideal state of immobilization by occlusion as indicated by a high ratio of activity and practically negligible leakage of enzyme can be realized.

Now, the present invention will be described more specifically with reference to working examples. It should be noted, however, that this invention is not restricted to the following examples.

EXAMPLE 1

A mixed solution of an enzyme and a photosensitive resin was prepared by diluting with 268 g of water 22.5 g of an aqueous solution containing in a concentration of 11.1% by weight of polymer obtained by incorporating 1.3 mol % of a styrylpyridinium group in a poly(vinyl alcohol) possessing a polymerization degree of 1,700 and a saponification ratio of 88% and then dissolving 1 g of invertase (produced by Seikagaku Kogyo K.K.) possessing an activity of 117 U/mg in the diluted aqueous solution. In the mixed solution, the weight ratio of the enzyme to the resin was 2:5.

Then, the mixed solution was sprayed at a flow rate of 1.7 ml/min into a drying chamber of a small spray drier (produced by Yamato Kagaku K.K. and marketed under trademark designation of "Palvis Minispray GA-21") in which air at a temperature of 25° C. and a relative humidity of 75% was heated to about 51° C. and supplied at a flow volume of 0.5 Nm$^3$/min as the drying gas. As a result, the mixed solution was dried in a few seconds.

The resultant dry powder was recovered in a glass vial from a collecting cyclone (GA-21) and exposed for 30 minutes to the light from five chemical lamps (20 W) kept at a distance of 10 cm to induce photo-crosslinking of the polymer and produce polymer particles.

The produced polymer particles, by observation under a scanning electron microscope, were found to be minute particles measuring 2 to 5 $\mu$m in diameter and possessing an average particle diameter of 2.5 $\mu$m. By the test of the Karl Fischer Technique, the particles were found to have a water content of 3.6%.

Then, 35 mg of the invertase-immobilized polymer particles (10 mg as invertase) were thrown in 90 ml of an aqueous solution containing sucrose in a concentration of 0.5 mol/liter and adjusted to pH 4.5 and the resultant mixture was heated at 30° C. to induce hydrolysis of the sucrose. When this mixture was stirred with a magnetic stirrer in a flask, the immobilized enzyme was dispersed in the liquid in an extremely short period. By observation under an optical microscope, the immobilized enzyme particles were found to swell with water to a degree of 10 to 20 $\mu$m.

From the reaction solution, 1-ml samples were taken along the course of time, each placed in 3 ml of hot water held in a test tube retained in a water bath at 95° C. to inactivate the invertase, filtered to separate the particles, and analyzed by ion-exchange chromatography. The results indicate that the hydrolysis proceeded on the first order with reference to the sucrose concentration and the reaction velocity constant was 0.0585 min$^{-1}$.

When the same amount of the invertase in the form of an aqueous solution, namely in an unimmobilized state, was used in the same reaction, the reaction proceeded on the first order with respect to the sucrose concentration and the reaction velocity constant was 0.0790 min$^{-1}$. By comparison of the two sets of numerical values, it is found that the enzyme immobilized by this invention manifested the activity at an extremely high ratio of 74%.

To find the amount of the unimmobilized enzyme adhering to the surface of the immobilized enzyme particles, the particles were washed with water and the washing was tested for activity. This washing was performed by repeating three times the procedure of stirring the same amount of the immobilized enzyme particles as in the aforementioned reaction in 8 ml of water for three minutes, centrifuging the stirred liquid to settle the particles and collecting the supernatant as the washing. It was consequently found that the washing exhibited only 0.36% of the activity of the particles showing that the particles had substantially no unimmobilized enzyme on the surface.

Then, to find the amount of the enzyme shed from the immobilized enzyme gel particles, the gel particles washed under the same conditions were used to initiate the reaction. The solution collected after 30 minutes of the reaction was filtered to remove the gel particles and the filtrate was tested for activity of the enzyme. As a result, the activity of the enzyme in the filtrate was only 0.12% of that of the gel particles, indicating that the separation of the enzyme was practically negligible.

COMPARATIVE EXPERIMENT

Enzyme-occluding polymer particles 20 to 100 μm in diameter were obtained by the suspension crosslinking method disclosed in Japanese Patent Public Disclosure SHO 61(1986)-128888.

When the polymer particles were tested for reaction velocity constant by following the procedure of Example 1, the ratio of activity was found to be 30%.

EXAMPLE 2

Rhizopus lipase polymer particles were obtained by following the procedure of Example 1, except that rhizopus lipase was used in place of the invertase. When the polymer particles were tested for activity with olive oil as a substrate, there were obtained highly desirable results.

EXAMPLE 3

The polymer particles of Example 1 were pelletized at 50° C. in a small fluidized-bed pelletizer, with the aqueous solution of 0.02 wt % of the polymer of Example 1 supplied as a binder at a rate of 0.5 ml/min and air supplied at a gradually increased feed volume of 0.02 to 0.1 Nm$^3$/min. Consequently, there were obtained secondary particles measuring 0.2 to 0.5 mm in diameter and possessing an average porosity of 55%. When the secondary particles were tested for reaction velocity constant by the procedure of Example 1, the ratio of activity was found to be 42%.

What is claimed is:

1. Dry enzyme-occluding polymer particles obtained by a method comprising the steps of:
    dissolving an enzyme in a aqueous solution of poly(vinyl alcohol) having a styrylpyridinium group or a styrylquinolinium group;
    spray-drying said aqueous solution to form dry particles having an average particles diameter in the range of 0.1 to 10 μm; and
    exposing said dry particles to actinic rays, thereby photo-crosslinking said dry particles to obtain said dry enzyme-occluding polymer particles.

2. The particles of claim 1, wherein said particles are pelletized.

3. The particles of claim 1, wherein during spray drying, the spray droplets have an average diameter of not more than 50 μm.

4. The particles of claim 3, wherein said average diameter of the spray droplets is not more than 20 μm.

5. The particles of claim 1, wherein the initial temperature of the current of air employed in the spray-drying step is within the rate of 30° to 80° C.

6. The particles of claim 1, wherein, in the spray drying step, drying of the spray droplets occurs within seconds.

7. The particles of claim 2, wherein the pellets prepared from the enzyme-occluding polymer particles have a porosity within the rage of 20-60%.

8. The particles of claim 1, wherein the poly(vinyl alcohol) having a styrylpyridinium group or a styrylquinolinium group contains these groups in an amount of 0.5 to 8 mol. % based on the vinyl alcohol units of the polymer.

9. A method for the production of dry enzyme-occluding polymer particles, comprising the steps of:
    dissolving an enzyme in an aqueous solution of poly(vinyl alcohol) having a styrylpyridinium group or a styrylquinolinium group;
    spray-drying said aqueous solution for a period of seconds to form dry particles having an average particle diameter ranging from 0.1 to 10 μm; and
    exposing said dry particles to actinic rays, thereby photo-crosslinking said dry particles to produce said dry enzyme-occluding polymer particles.

10. The method of claim 9, which further comprises pelletizing said dry enzyme-occluding polymer particles.

11. The method of claim 9, which further comprises pelletizing said dry particles before the step in which the dry particles are exposed to actinic rays.

* * * * *